United States Patent
Page et al.

(10) Patent No.: US 9,534,989 B2
(45) Date of Patent: Jan. 3, 2017

(54) DEVICES, SYSTEMS AND METHODS FOR ELUTION OF PARTICLES FROM FLAT FILTERS

(71) Applicant: InnovaPrep LLC, Drexel, MO (US)

(72) Inventors: Andrew Edward Page, Smithton, MO (US); David Scott Alburty, Drexel, MO (US); Alec D. Adolphson, Raymore, MO (US); Pamela S. Murowchick, Lenexa, KS (US); Zachary A. Packingham, Drexel, MO (US)

(73) Assignee: INNOVAPREP, LLC, Drexel, MO (US)

( * ) Notice: Subject to any disclaimer, the term of this patent is extended or adjusted under 35 U.S.C. 154(b) by 270 days.

(21) Appl. No.: 14/084,403

(22) Filed: Nov. 19, 2013

(65) Prior Publication Data

US 2014/0076071 A1    Mar. 20, 2014

Related U.S. Application Data

(63) Continuation of application No. 12/883,137, filed on Sep. 15, 2010, now Pat. No. 8,584,536.

(51) Int. Cl.
   *G01N 1/22*     (2006.01)
   *G01N 1/40*     (2006.01)

(52) U.S. Cl.
   CPC ............ *G01N 1/2205* (2013.01); *G01N 1/2273* (2013.01); *G01N 2001/4088* (2013.01)

(58) Field of Classification Search
   CPC .................................................. G01N 1/2205
   USPC ..... 73/864.24, 864.25, 864.23, 28.01, 28.05, 73/28.06; 95/75
   See application file for complete search history.

(56) References Cited

U.S. PATENT DOCUMENTS

| | | | | |
|---|---|---|---|---|
| 3,766,715 A * | 10/1973 | Archer | ................ | G01N 27/16 55/283 |
| 3,984,221 A * | 10/1976 | Cotton, Jr. | ......... | B01D 46/0005 55/484 |
| 4,134,741 A * | 1/1979 | Elsbernd | ................ | B03C 3/88 134/22.19 |
| 5,404,762 A * | 4/1995 | Rodgers | ................ | B01D 46/10 73/863.25 |
| 6,777,228 B2 * | 8/2004 | Lejeune | ............... | G01N 1/2273 435/288.6 |
| 2006/0278086 A1 * | 12/2006 | Inagaki | ............. | B01D 46/0001 96/223 |

* cited by examiner

*Primary Examiner* — Peter Macchiarolo
*Assistant Examiner* — Nathaniel Kolb
(74) *Attorney, Agent, or Firm* — Mozzam & Associates, LLC

(57) ABSTRACT

Devices, systems and methods are disclosed which relate to using a wet foam elution method for removal of particles from a flat filter. Particles are captured from the atmosphere onto the flat filter. The flat filter is then placed into an extractor which passes a stream of wet foam through the flat filter. Expansion of the foam works to efficiently remove captured particles. The foam flows from the filter along with the captured particles into a sample container. Once in the sample container, the foam quickly breaks down leaving an analysis ready liquid sample.

20 Claims, 8 Drawing Sheets

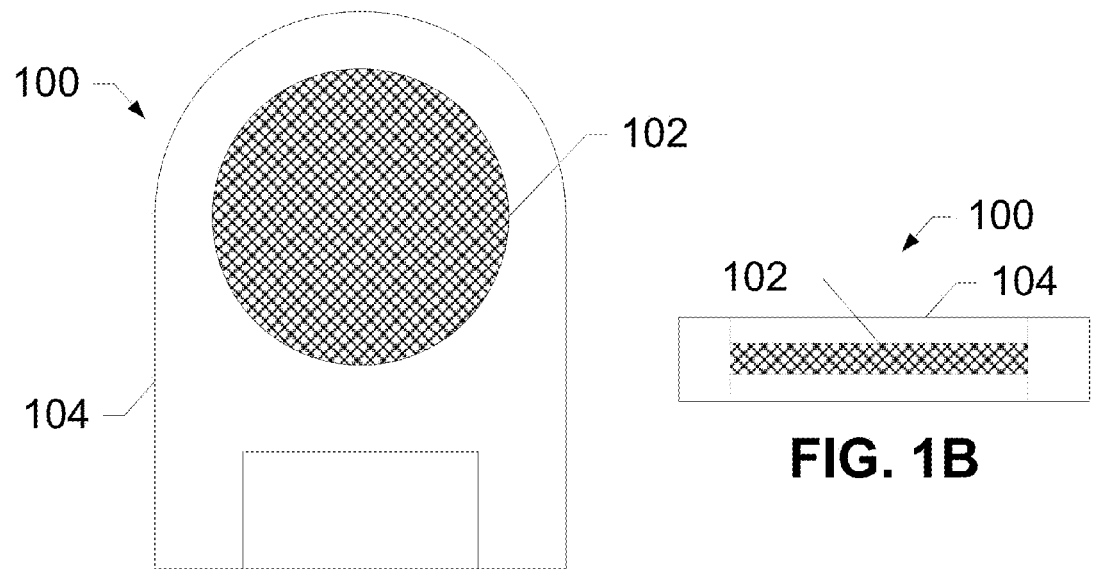
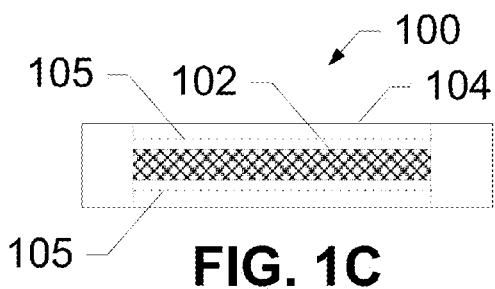
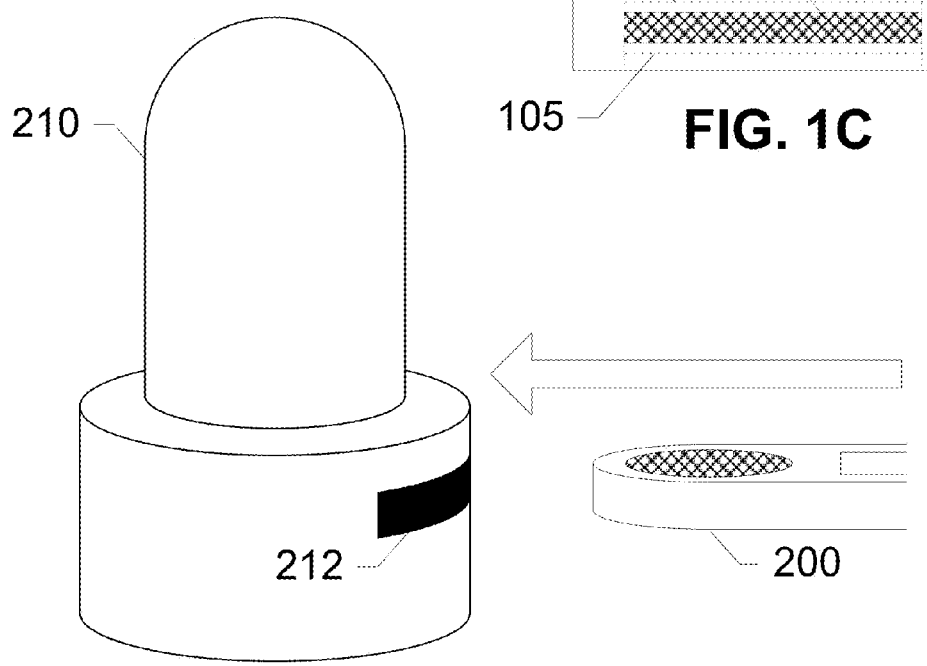

DEVICES, SYSTEMS AND METHODS FOR ELUTION OF PARTICLES FROM FLAT FILTERS

This U.S. Patent Application is a continuation of U.S. patent application Ser. No. 12/883,137, filed Sep. 15, 2010, now U.S. Pat. No. 8,584,536; which claims priority to U.S. Provisional Patent Application Ser. No. 61/277,119, filed Sep. 21, 2009, and to U.S. Provisional Patent Application Ser. No. 61/338,051, filed Feb. 16, 2010; the contents of which are hereby incorporated by reference herein in their entirety into this disclosure.

BACKGROUND OF THE INVENTION

Field of the Invention

The present invention relates to the field of particle collection. More particularly, the present invention relates to collection of particles from the air onto filters and the rapid, efficient elution of these particles from flat filters into a liquid sample.

Background of the Invention

The difficulties of detecting and quantifying particles in air and liquids are well known. Existing systems all begin to fail as concentration decreases until, eventually with diminished concentrations of analyte, there is an inability to detect at all. This poses a significant problem to national security where, for example, the postal anthrax attacks of 2001 and the subsequent war on terrorism have revealed shortcomings in the sampling and detection of biothreats. The medical arts are similarly affected by the existing limits on detection, as are the environmental sciences.

In the fields of biodefense and aerosol research it is common to collect aerosols into a liquid sample using a wet cyclone or similar device. The aerosol is collected into an aqueous sample so that subsequent analysis of biological particles can be performed using standard techniques that primarily require that the sample be contained in liquid. These "wet" collectors have many failings including difficulty in maintaining a set fluid volume and difficulties with buildup of particle matter in the device.

Dry filters have long been used for collection of aerosols, as well as for collection of particles from liquids. However, dry filters fail for the use of identifying biological particles primarily because it is difficult to remove the particles into a liquid. Methods for removing particles from flat or fiber-based depth filters are common but are tedious and often very inefficient. What is needed is a system, method, or device to efficiently remove particles from a flat filter without corrupting the captured sample.

SUMMARY OF THE INVENTION

The present invention includes systems, methods, and devices disclosed herein for using a wet foam elution method for removal of particles from a flat filter. Particles are captured from the atmosphere onto the flat filter. The flat filter is then placed into an extractor which passes a stream of wet foam through the flat filter. Expansion of the foam works to efficiently remove captured particles. The foam flows from the filter along with the captured particles into a sample container. Once in the sample container, the foam quickly breaks down leaving an analysis ready liquid sample.

In one exemplary embodiment, the present invention is a system for collecting and extracting a sample from an aerosol. The system includes a collector, a flat filter coupled with the collector so that air flows through the flat filter, an extractor for backflushing the flat filter with an elution foam, a container for collecting the foam once it is backflushed through the flat filter. The flat filter is inserted into the collector to collect the sample from the aerosol, then the foam is used to backflush the flat filter into the container.

In another exemplary embodiment, the present invention is a method for collecting and extracting a sample from an aerosol. The method includes inserting a flat filter into a collector, collecting particles onto the flat filter, and backflushing the filter with elution foam into a sample container.

In yet another exemplary embodiment, the present invention is a device for collecting and extracting a sample from an aerosol. The device includes a filter material, a cassette housing encasing the filter material such that the surface of the filter material is substantially exposed on both sides. The cassette housing is adapted to be sealingly inserted into a collector to collect the sample from the aerosol. The cassette housing is adapted to be sealingly inserted between a nozzle and a sample container, the nozzle for an elution foam used to backflush the flat filter into the sample container.

BRIEF DESCRIPTION OF THE DRAWINGS

FIG. 1A shows a flat filter for aerosol-to-liquid concentration, according to an exemplary embodiment of the present invention.

FIG. 1B shows a side-view of a flat filter for aerosol-to-liquid concentration, according to an exemplary embodiment of the present invention.

FIG. 1C shows a side-view of a flat filter for aerosol-to-liquid concentration, according to an exemplary embodiment of the present invention.

FIG. 2 shows a collector which complements a flat filter, according to an exemplary embodiment of the present invention.

DETAILED DESCRIPTION OF THE INVENTION

Figure 3A:
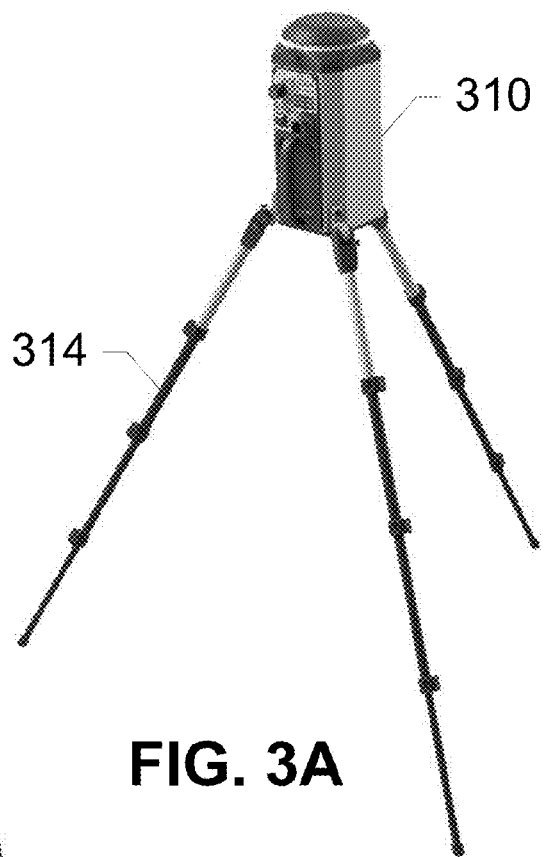
FIG. 3A shows a collector, according to an exemplary embodiment of the present invention.

The present invention includes systems, methods, and devices disclosed herein for using a wet foam elution method for removal of particles from a flat filter. Particles are captured from the atmosphere onto the flat filter. The flat filter is then placed into an extractor which passes a stream of wet foam through the flat filter. Expansion of the foam works to efficiently remove captured particles. The foam flows from the filter along with the captured particles into a sample container. Once in the sample container, the foam quickly breaks down leaving an analysis ready liquid sample. In one exemplary embodiment, an extractor is designed to work with a flat filter substantially in a condition as supplied by commercial filter producers. In another exemplary embodiment, the flat filter is held within a housing that provides a pressure seal around the perimeter of the flat filter to facilitate elution of the captured particles from the flat filter under pressure.

Foam has been used and studied extensively for use in semiconductor cleaning, radioactive particle removal, and for decontamination of biological agents. Foams are also frequently used during hydrocarbon exploration. The most common use is in the area of enhanced oil recovery. Due to the high viscosity of foams, they exhibit reduced channeling thereby sweeping more oil out of porous media. This same characteristic makes foam ideal for extraction of multiple fiber concentration cells. It is well known that channeling or non-uniform flow distribution takes place in hollow fiber modules that contain multiple fibers. Channeling is dependent on inlet manifold design, Reynolds number, pressure drop, and other issues such as irregularity in fiber diameter. In short, channeling is difficult to control and is almost certainly a factor during recovery of organisms from multiple fiber concentration units with aqueous extraction fluids.

The flow of foams in small channels is a complex subject. Several research teams have recently studied this subject and determined that uniform foams in a capillary exhibit plug flow and self-lubricate with a very narrow lubricating layer thickness on the order of 10 µm or less. The foam moves as a rigid body lubricated by water generated by breaking foam at the wall. Because core flow is absent and the lubricating layer is thin, the foam is able to act at the fiber surface to sweep away the captured particles. Further, energy created by breaking bubbles may enhance particle removal from the hollow fiber surface. The majority of the bubbles in the carbonated, extraction foam burst soon after release from the concentration cell, returning the foam to a liquid and allowing for transfer to the detector as an aqueous sample. Most of the foam has returned to a liquid within thirty seconds.

For the following description, it can be assumed that most correspondingly labeled structures across the figures (e.g., 200 and 300, etc.) possess the same characteristics and are subject to the same structure and function. If there is a difference between correspondingly labeled elements that is not pointed out, and this difference results in a non-corresponding structure or function of an element for a particular embodiment, then that conflicting description given for that particular embodiment shall govern.

FIG. 1A shows a flat filter 100 for aerosol-to-liquid concentration, according to an exemplary embodiment of the present invention. Flat filter 100 includes a filter material 102 and a cassette housing 104. Filter material 102 is an electret material, such as FILTRETE (3M), which develops charge when air flows past the filter fibers. Cassette housing 104 holds filter material 102 in place during collection and elution. Cassette housing 104 is designed to complement a collector having an opening for receiving flat filter 100. A collector, which generates air flow through an aerosol chamber, has a gap in the aerosol chamber for flat filter 100. When flat filter 100 is inserted, cassette housing 104 closes the gap and forces air through filter material 102. Cassette housing 104 preferably creates seals between the aerosol chamber and cassette housing 104 to ensure containment of air.

The cassette housing may also complement other equipment used in the process of aerosol-to-liquid concentration such as an extractor. The same housing may be used provided the collector and the extractor accept the same design. An extractor preferably requires seals as well. The cassette housing may be made of plastic, metal, or any other solid, durable materials. Materials that can be easily molded into shapes complementary to collectors and extractors are preferable. Those having skill in the art will readily recognize other materials upon reading this disclosure. There are many types of filters that may be used in the flat filter. However, electret filters are preferable because the charges substantially increase the efficiency of the filter and allow for the use of lower pressure drop filters. In other exemplary embodiments, filter material is cut from standard off-the-shelf 3M Ultimate Allergen Reduction Filtrete TM filters, and placed into 47 mm cassette housings. In other exemplary embodiments, a filter backing screen is coupled with the cassette housing to hold the filter material in place while fluids are forced through.

FIG. 1B shows a side-view of a flat filter 100 for aerosol-to-liquid concentration, according to an exemplary embodiment of the present invention. Flat filter 100 includes filter material 102 held inside cassette housing 104. Cassette housing 104 holds filter material 102 around the edges, leaving the substantial portion of filter material 102 exposed for particle collection.

FIG. 1C shows a side-view of a flat filter 100 for aerosol-to-liquid concentration, according to an exemplary embodiment of the present invention. Flat filter 100 includes filter material 102 and two filter backing screens 105 held inside cassette housing 104. Filter backing screens 105 hold filter material in place while air is forced through during collection, and while foam is forced through during extraction. Each filter backing screen 105 is a simple screen which uses just enough material to hold filter material 102 in place. In this way filter backing screens 105 provide support without substantially interfering with airflow or collection.

Though the filters of FIG. 1 are designed for aerosol collection, a substitute of filter material can make the filter appropriate for liquid collection. For use in liquid collection, the filter material has an electrostatic or Zeta potential effect to efficiently collect target particles. This attracts particles of interest to the filter material for efficient collection. These filter materials include electrically enhanced, depth, and membrane filter material. The electrically enhanced filter material is most commonly an electret filter material. Depth filter material includes glass fiber, polymer fiber, cellulose fiber material, or other such material. Glass fiber filters in particular are known to have attractive forces towards bacteria in solutions and can be used to efficiently collect these organisms while allowing other interfering particles to pass. One having ordinary skill in the art would recognize how to substitute different filters into the devices and systems according to the present invention after consideration of the present disclosure.

FIG. 2 shows a collector 210 which complements a flat filter 200, according to an exemplary embodiment of the present invention. Collector 210 includes an opening 212 where flat filter 200 is inserted. Flat filter 200 is slidably inserted into collector 210 through opening 212 for collection of particles from the air. Once inserted, collector 210 draws air from its environment through flat filter 200, where particles attach to flat filter 200.

In exemplary embodiments of the collector, a vacuum pump is used to draw air through the flat filter at a rate of 200 Lpm. The opening has many forms across many exemplary embodiments. In some exemplary embodiments, the opening is a lid which opens to expose the placement of the flat filter. In other exemplary embodiments, the opening is just large enough to slide the cassette housing into the collector. In further exemplary embodiments, a tray slides out for reception of the flat filter, then slides back inside the collector for collection. Other forms of the opening will become readily recognizable to those having skill in the art upon reading this disclosure.

FIG. 3A shows a collector 310, according to an exemplary embodiment of the present invention. Collector 310 includes legs 314 for holding collector 310 in the air for efficient collection. Legs 314 are collapsible making collector 310 portable. Collector 310 is also battery powered.

Other exemplary embodiments of the collector include features such as a built-in carry handle, an omni-directional aerosol inlet, a mass flow sensor for consistent sampling rates, etc. Some exemplary embodiments are designed for lab use, while others are designed for more rugged field use. It is common for exemplary embodiments to include military specifications for extreme environments.

Figure 3B:
FIG. 3B shows a collector with an inserted flat filter, according to an exemplary embodiment of the present invention.

FIG. 3B shows collector 310 with an inserted flat filter 300, according to an exemplary embodiment of the present invention. Collector 310 includes lid 312, which is opened to insert flat filter 300. Once flat filter 300 is inserted, lid 312 is closed and collection may begin.

Figure 4:
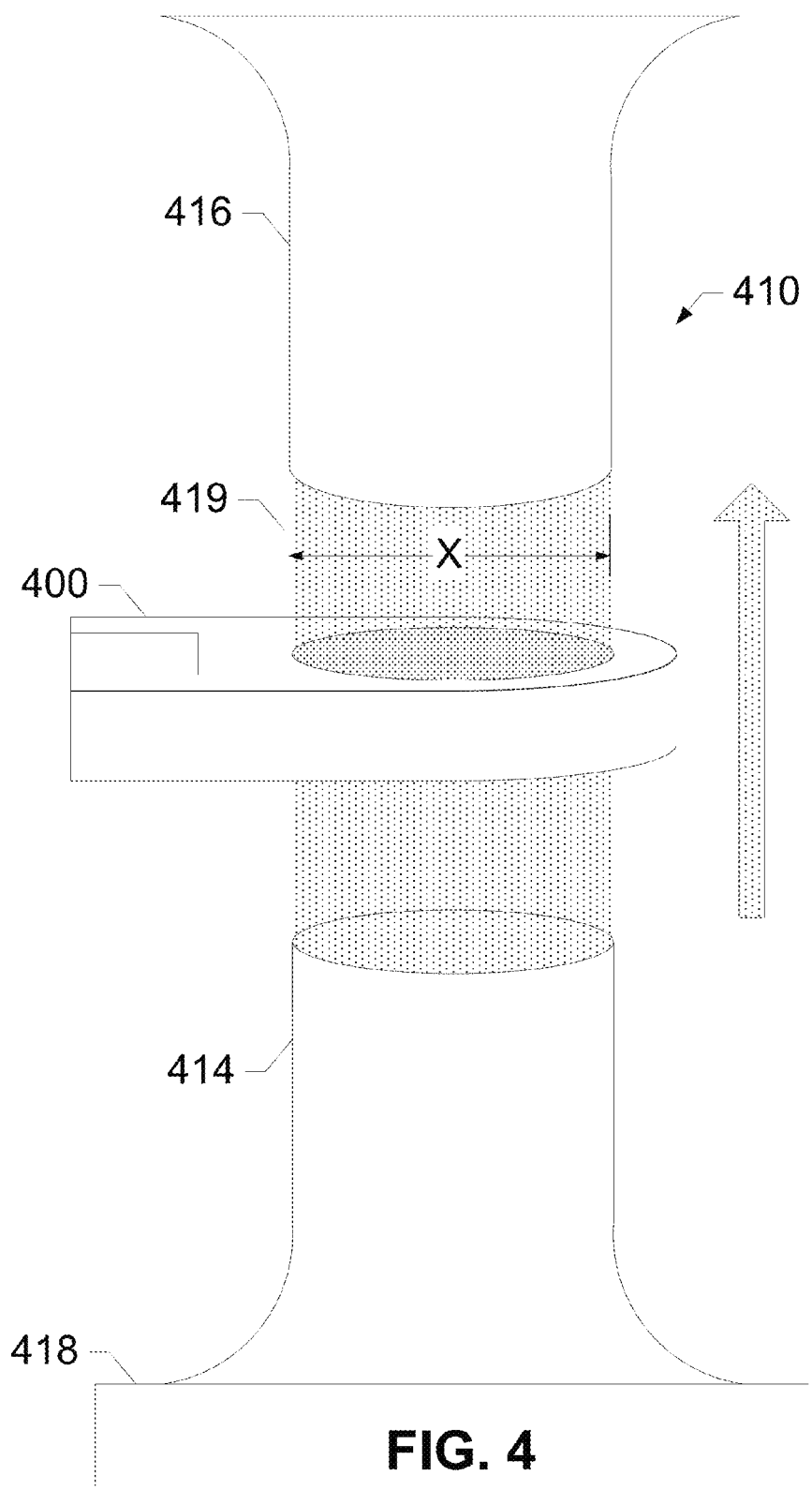
FIG. 4 shows the inside of a collector with an inserted flat filter, according to an exemplary embodiment of the present invention.

FIG. 4 shows the inside of a collector 410 with an inserted flat filter 400, according to an exemplary embodiment of the present invention. Collector 410 includes an aerosol chamber intake 414, an aerosol chamber exhaust 416, a vacuum pump 418, and inserted flat filter 400. When vacuum pump 418 is activated, air flows from the vacuum pump into aerosol chamber intake 414. Flat filter 400 is inserted into the gap between aerosol chamber intake 414 and aerosol chamber exhaust 416. Here, air is forced through flat filter 400, where flat filter 400 captures particles in the air. Once through flat filter 400, air travels into aerosol chamber exhaust 416, where it escapes back into the atmosphere. Flat filter 400 uses a diameter 419 which matches the aerosol chamber to maximize the efficiency of the airflow. Diameter 419 determines the velocity of air when flowing through collector 410. A higher air velocity requires more power, and results in a lower efficiency. The relatively large diameter 419 of flat filter 400 provides for a reduced airflow velocity through the filter allowing for more efficient collection and reduced power consumption.

For purposes of illustration there is a distance shown between the sides of flat filter 400 and aerosol chamber intake 414, as well as aerosol chamber exhaust 416. However, these distances are for illustrative purposes only, and in exemplary embodiments most flat filters fit tight against the aerosol chamber intake and exhaust to help seal the aerosol chamber.

Though the collector in FIG. 3 is an aerosol collector, a liquid collector has a similar setup to that of FIG. 4. Liquid collectors have a liquid intake, a liquid exhaust, and a flat filter in between. When filtering relatively clean liquids hollow fiber filters or flat membrane filters can be readily used to capture particles of interest. However, dirty environmental samples, food homogenate samples, and clinical fluid samples that contain large numbers of interfering particles will readily blind or significantly reduce the flow rate of these filters. By using a fibrous depth filter buildup of particles on the filter surface is reduced significantly; however, efficient capture of bacteria and viruses can also be significantly reduced. Still, depth filters of sufficiently tight structure are capable of efficiently capturing bacteria, spreading the load of interfering particles over a thicker layer than is seen when using membrane filters, thus the flow rate is not reduced as rapidly when using these filter types. Certain filter types also provide zeta potential or electrostatic forces towards bacteria, viruses, and other particles of interest while still allowing interfering particles to pass through or while not allowing them to build up into a single blinding layer on the filter surface. Zeta potential filters, nanoceram filters and even some very standard filter types like glass fiber depth filters exhibit these characteristics in certain instances. Using these depth filter types, and especially those that exhibit zeta potential or attractive forces to the particles of interest, along with wet foam elution provides a means of rapidly concentrating bacteria and viruses from large volumes of liquids containing large amounts of interfering particles without significant reduction in the collector flow rate.

Figure 5:
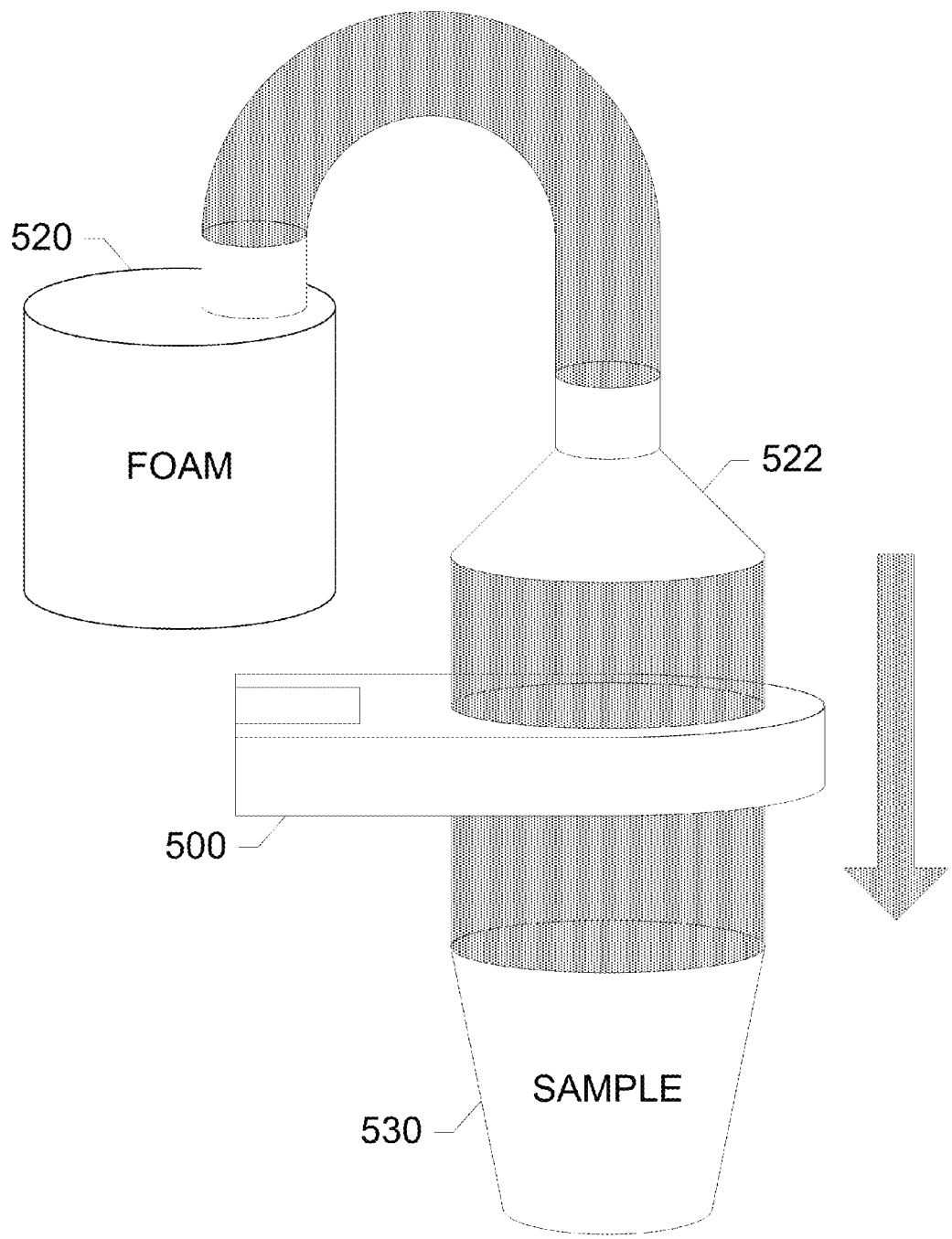
FIG. 5 shows components for extraction of a flat filter, according to an exemplary embodiment of the present invention.

FIG. 5 shows components for extraction of a flat filter 500, according to an exemplary embodiment of the present invention. These components include a source of foam 520, a nozzle 522, a sample container 530, and flat filter 500. Source of foam 520 is connected to nozzle 522 through a tube, hose, etc. Nozzle 522 is designed to fit the diameter of flat filter 500. Sample container 530 has a matching diameter as well. Flat filter 500 is sealed between nozzle 522 and sample container 530, but may contain vent openings to allow for the escape of gas that takes place as the wet foam breaks down. Foam flows from source 520 through nozzle 522 where it washes the captured particles from flat filter 500 into sample container 530 through a technique called backflushing. In order to correctly backflush flat filter 500, flat filter 500 must be oriented so that the foam flows through the side of flat filter 500 that was facing the aerosol chamber exhaust. The particles are captured on the side of flat filter 500 that was facing the aerosol chamber intake. It is easier to wash the captured particles back off of the surface upon which they were captured, rather than try to wash the captured particles through the filter and out the other side. Orientation of flat filter 500 is kept constant through FIG. 2 (200), FIG. 4 (400), and FIG. 5 in order to illustrate this concept.

For purposes of illustration there is a distance shown between the sides of flat filter 500 and nozzle 522, as well as sample container 530. However, these distances are for illustrative purposes only, and in exemplary embodiments most flat filters fit tight against the nozzle and sample container to help seal the aerosol chamber. Vents may also be present to help relieve pressure that builds up in the system from breakdown of the foam. The vent may be simple holes in the sample container or may be covered by hydrophobic vent material to reduce the potential of aerosol production during extraction.

A backflush with wet foam is the preferred method of extracting particles from flat depth type or fibrous type filters and may also be used for extraction of flat membrane type filters. For a number of reasons the use of wet foam is preferred. Two primary reasons for the preference of foam for elution are (1) that a small volume of liquid may be used to create a large volume of wet foam, thus allowing for smaller elution volumes, and (2) the created foam is much more viscous than the starting surfactant solution, thus allowing for improved passage of the foam through the filter while contacting all fibers within the filter. Backflushing of depth or fibrous filters, especially those with a very open pore structure, with a liquid is in general very inefficient due to channeling of the liquid through the center of the filter. Channeling of the liquid dramatically reduces the percentage of the filter that is contacted, unless extremely large liquid volumes are used. As a general rule-of-thumb liquids are expanded approximately 5 to 6 times when a wet foam is produced through the processes proposed here, but expansion volumes in the range of 2 to over 20 times are possible. Based on an expansion of 5 times and a significant increase in viscosity of the liquid it is common that wet foam elution of depth or fibrous type filters can be performed with high efficiency with volumes approximately $1/10^{th}$ or less of the volume as would be required with using a liquid elution fluid. Since the boundaries of the bubbles present in the foam must remain intact to remain as foam, the boundaries of the bubbles at the interface of the flat filter and the extraction foam must always be substantially touching. As the foam proceeds through the flat filter, it sweeps the captured particles into a sample container. When the foam is extracted into the sample container and collapses, the remaining product is a small volume of liquid. This volume can be in a range of less than 5 µL to 1 L or more. In exemplary embodiments, the foam may be made in a separate container and then injected to sweep the sample of captured particles from the filter into the sample container. However, a sample loop or volumetric sample dispensing reservoir may also be used to measure the amount of liquid used to make the foam. In a preferred embodiment the foam is produced by holding a buffered surfactant solution under a head pressure of carbon dioxide and then releasing a volume by opening a timed valve. By controlling both the carbon dioxide pressure and the time that the valve is open the volume of liquid dispensed can be tightly controlled. In other exemplary embodiments, the extractor components are housed in an extractor unit designed to receive a flat filter. In addition to surfactant foams that are generated by mixing air and a surfactant solution, the foam may be generated with a carbonated surfactant solution. Following carbonation, the solution is agitated by dispensing through an orifice, frit, filter, or capillary tube. The surfactant foam extraction methods described herein can also be used for extraction and cleaning of other collection surfaces in aerosol samplers and collectors. The use of foam to extract these surfaces can provide a significant increase in extraction efficiency and significant decrease in final sample volume. Such extraction methods are disclosed in U.S. patent application Ser. No. 12/814,972, which is hereby incorporated by reference herein in its entirety.

The wet foam elution method uses standard buffer solutions such as phosphate buffered saline (PBS) or tris buffered saline with a surfactant or protein added to allow the solution to foam. A few of the surfactants and proteins tested to date include Triton X-100, Tween 20, Tween 80, and bovine serum albumin. Concentrations of Triton or Tween must generally be 0.01% or higher to insure adequate levels of foam. A PTFE-lined, Sulfinert treated or appropriate plastic pressure reservoir is filled with wet foam elution buffer and carbon dioxide is added through a fritted bubbler until a head pressure of 100 to 300 psi is attained. In another embodiment a magnetic stir bar or other means of stirring is used within the pressure reservoir or a rapid injection of carbon dioxide may take place through a section of tubing—in each case the goal of the injection and mixing method is to increase the exposed surface area of the liquid and thus increase the rate by which the carbon dioxide is absorbed. The reservoir, or foam source, is then held at constant pressure using a regulator. The carbon dioxide is now in solution with the liquid containing 3 to 20 times its own volume of carbon dioxide at ambient pressure. Controlled volumes of the liquid are dispensed with a timer controlled dispensing valve. When the liquid is released through the dispensing valve and returns to atmospheric pressure a large percentage of the carbon dioxide comes out of the solution as small bubbles, creating wet foam. The wet foam can be swept through the bore of hollow fiber filters, the interstitial spaces in flat depth filters, such as a FILTRETE filter, or along a length of surface while contained in an extraction wand. Shortly after extraction the foam returns to a liquid making it available for further processing or analysis.

In exemplary embodiments, a single shot of wet foam ranging from 0.01 seconds to 10 seconds is used to elute the filter. A second extraction of each filter can be performed in the same way. A nominal extraction volume of 25 mL is used for these flat filter extractions.

Though the system of FIG. 5 is shown extracting a sample taken from an aerosol, this system is also used to extract samples taken from liquids or surfaces. When extracting from a depth type filter, especially Zeta potential filters, nanoceram filters, glass fiber depth filters, etc., the wet foam offers the same advantage as it does with the electret filters used for aerosol collection. The wet foam elution allows for the elution foam to efficiently contact the entire filter surface and remove the captured particles into a small volume.

Figure 6:
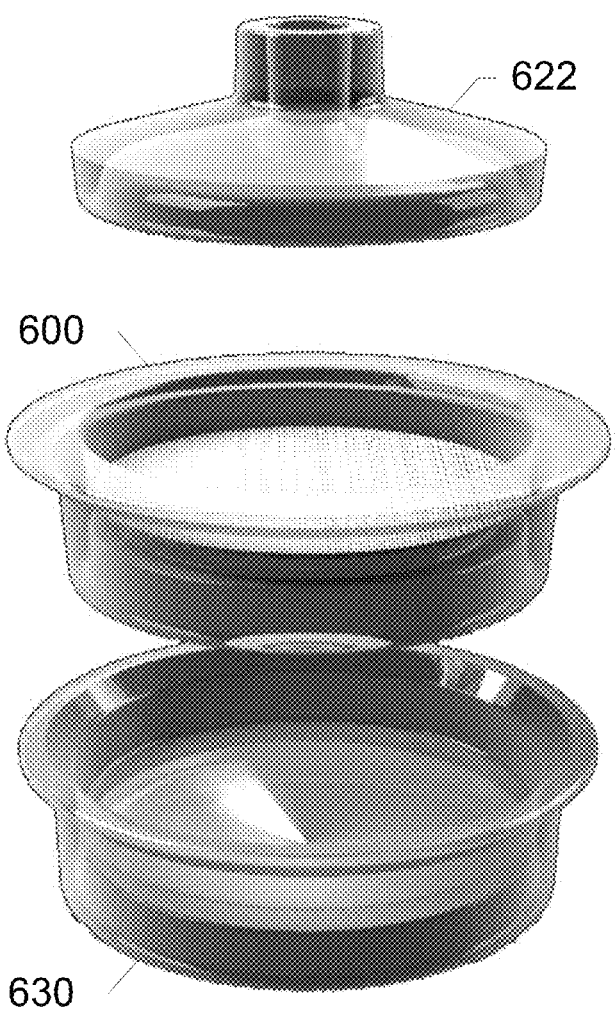
FIG. 6 shows an extractor, according to an exemplary embodiment of the present invention.

FIG. 6 shows an extractor, according to an exemplary embodiment of the present invention. The extractor includes a nozzle 622, a flat filter 600, and a sample container 630. Each piece is designed to fit sealingly together with flat filter 600 in between nozzle 622 and sample container 630. Nozzle 622 can be connected to a foam source in order to complete the extraction.

Figure 7:
FIG. 7 shows a pressurized foam container, according to an exemplary embodiment of the present invention.

FIG. 7 shows a pressurized foam container 720, according to an exemplary embodiment of the present invention. Pressurized foam container 720 includes an elution foam solution 726 inside a pressurized container 724. During extraction, pressurized foam container 720 is inserted into the nozzle of an extractor, such as nozzle 622 in FIG. 6. Once inserted, a release valve 728 is triggered which releases elution foam solution 726. As elution foam solution 726 is released, it expands into foam as it washes through the flat filter and into the sample container. Pressurized container 724 is made of acrylic in this exemplary embodiment. However those having ordinary skill in the art will recognize other suitable materials upon reading this disclosure.

The pressurized foam container is filled by one of two methods. The first of the methods is to connect the device to a fluid line connected to a large elution foam solution reservoir held under carbon dioxide head pressure. After connecting to the fluid reservoir a valve is opened and the elution foam solution fills the pressurized foam container. The second method uses a timed valve to dispense a set volume of elution foam solution into the pressurized foam container. In this case the pressurized foam container is only partially filled with elution foam solution and the head pressure in the pressurized foam container is used to push foam through the flat filter. In some exemplary embodiments, the valve is a self-opening female luer lock valve. The valve remains closed until it is connected to a male luer lock valve. In other exemplary embodiments the self-opening female luer lock valve is replaced with other self-opening valve types, such as male or female aerosol-type valves including Polyurethane foam-type valves and Kemp valves. The self opening valves may be continuous release or dosing valves that release a set volume when actuated. In other exemplary embodiments the valve is replaced with a puncture surface and the filter extractor assembly contains a sharp that punctures the surface when connected thereby releasing the extraction fluid.

Figure 8:
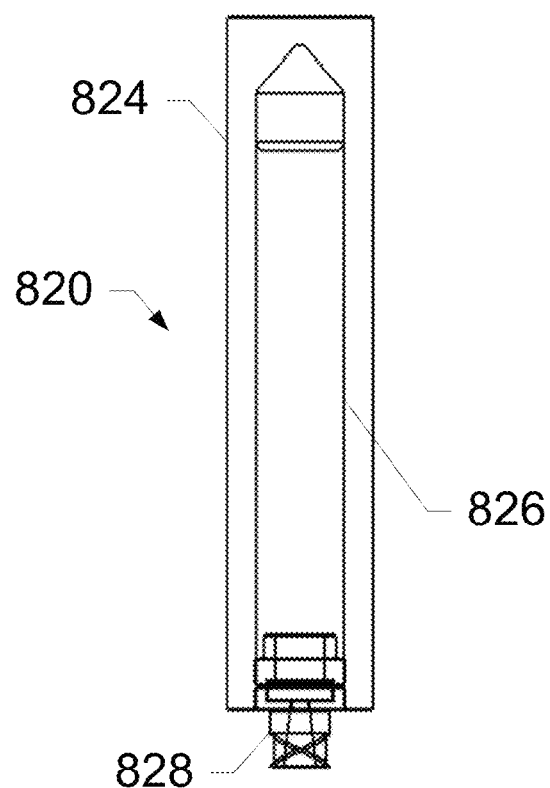
FIG. 8 shows a schematic view of a pressurized foam container, according to an exemplary embodiment of the present invention.

FIG. 8 shows a schematic view of a pressurized foam container 820, according to an exemplary embodiment of the present invention. Pressurized foam container 820 includes an elution foam solution 826 inside a pressurized container 824 including a release valve 828. Release valve 828 is a self-opening female luer lock valve. Once release valve 828 is triggered, elution foam solution 826 is released and expands into foam.

Pressurized container 824 is made of acrylic, but other materials are suitable. Some exemplary embodiments use metals to store the elution foam solution while others use strong plastics. Due to the permeability of some plastics to carbon dioxide and other gases the plastics may be coated with or bonded to non permeable materials, such as those used in polyethylene terephthalate bottles commonly used for carbonated beverages. There are also many ways to trigger the release valve. In some exemplary embodiments, the release valve is simply pushed into the extractor. In other exemplary embodiments, the release valve is twisted to trigger the release of foam. In these exemplary embodiments, the release valve may have grooves that complement the grooves of a nozzle such that the whole pressurized container is twisted with respect to the extractor to trigger the release valve.

Figure 9:
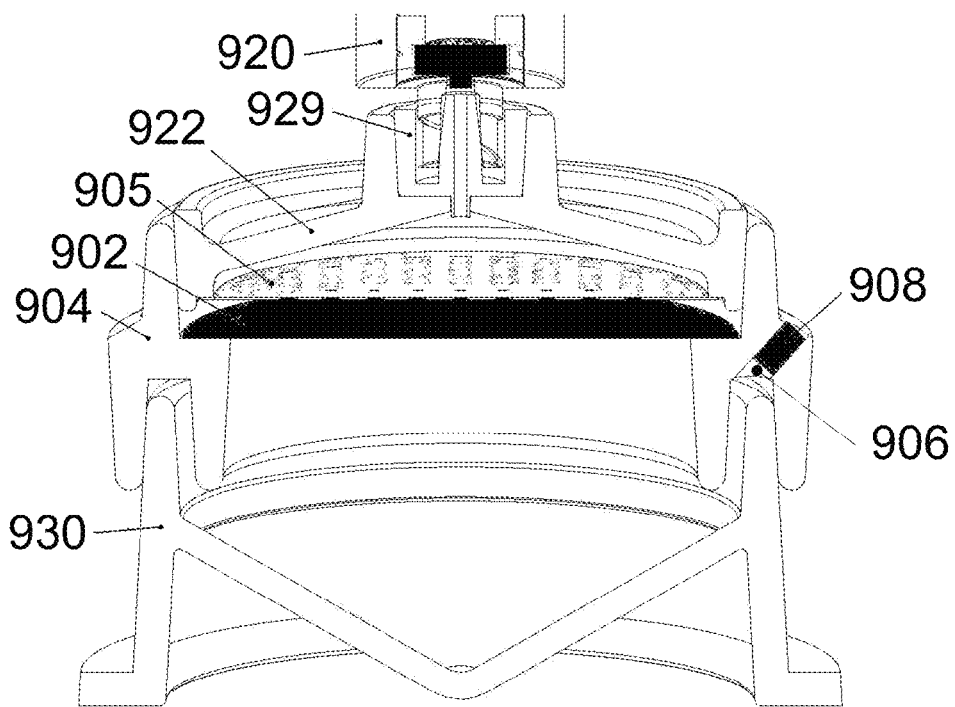
FIG. 9 shows a schematic view of an extractor, according to an exemplary embodiment of the present invention.

FIG. 9 shows a schematic view of an extractor, according to an exemplary embodiment of the present invention. The extractor includes a pressurized foam container 920 with female luer lock valve connected to a nozzle 922 with male luer lock 929, a filter backing screen 905, a filter material 902, a cassette housing 904, an aerosol vent 906, an aerosol filter 908, and a sample container 930. These components are designed to sealingly fit together with cassette housing 904 between nozzle 922 and sample container 930. At the top is pressurized foam container 920 with female luer lock valve, shown connected to a male luer lock 929 at the top of the cartridge. When connected to the cartridge a self-opening female luer lock valve on the hand held extraction device opens and the wet foam is released. The foam travels through filter backing screen 905 and filter material 902, and is captured in sample cup 930. During extraction, foam is forced into the extractor. Obstructing devices may be added to nozzle 922 to improve spreading of the wet foam prior to contact with filter material 902. Aerosol vent 906 allows pressure produced due to the off gassing of carbon dioxide from the wet foam, and due to carbon dioxide found in the head space of container 920, to vent to the outside without releasing aerosols that may be produced during extraction. Aerosol filter 908 prevents collected particles from escaping sample container 930 during extraction.

It takes less than five seconds for the extraction process to take place and then up to an additional sixty seconds for a majority of the remaining elution foam solution to finish dripping from filter material 902 and for the wet foam to break down into sample container 930. In this configuration filter material is a 42 mm diameter electret filter and the final liquid sample volume is 6 to 7 mL. The standard pressurized foam container 920 used with this system has an internal volume of 10 mL. This provides for 8 mL of extraction fluid plus 2 mL of head space with carbon dioxide. This provides some gas pressure to push the foam through the extractor and into sample container 930. Filter material 902 and a cassette housing 904 have a hold up volume of a little more than 1 mL generally, so 8 mL provides sufficient fluid to give a final volume of 6 to 7 mL.

The components of the extractor in FIG. 9 simply snap together. To improve the strength of the connections between components, exemplary embodiments employ circumferential lips and complementary circumferential grooves between components. When one component is snapped into another, the component is pressed until the lip is inserted into the groove. In other embodiments, the components have threads so that they can be screwed into one another for greater connection strength and reduced opportunities for leakage of fluid or aerosols. Further exemplary embodiments employ tabs on one component and grooves on another such that the tabbed component, when oriented correctly, slides into the grooved component and is twisted to lock the components together, such as how the cap of a medicine bottle attaches to its container.

Figure 10:
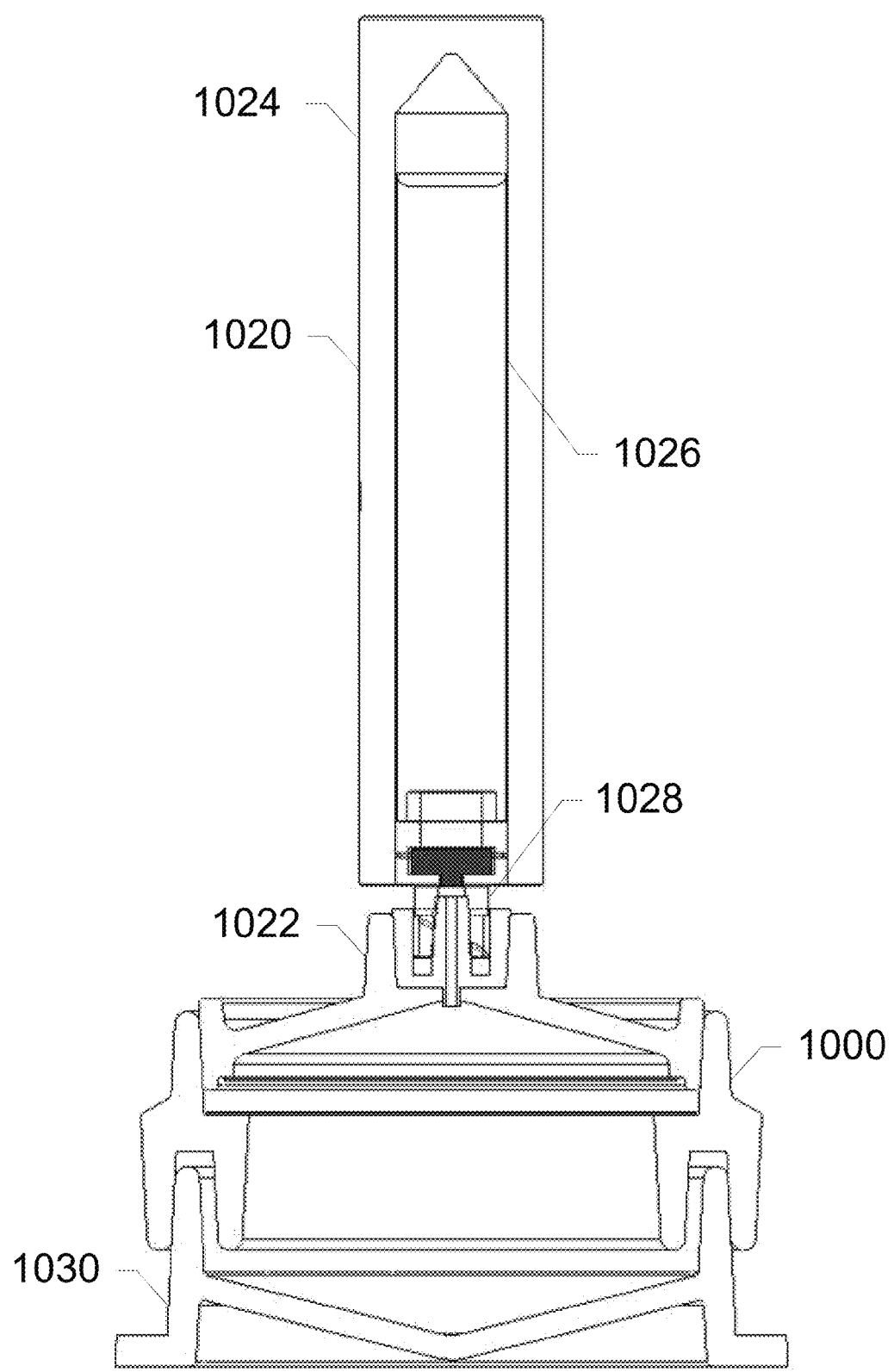
FIG. 10 shows a pressurized foam container combined with an extractor, according to an exemplary embodiment of the present invention.

FIG. 10 shows a pressurized foam container 1020 combined with an extractor, according to an exemplary embodiment of the present invention. Pressurized foam container 1020 includes an elution foam solution 1026 held within a pressurized container 1024, and a release valve 1028. Release valve 1028 is inserted into nozzle 1022 which, along with flat filter 1000 and sample container 1030, makes up the extractor. The insertion of release valve 1028 into nozzle 1022 releases elution foam solution 1026. This pressure release causes elution foam solution 1026 to turn to foam as it washes through nozzle 1022, filter 1000, and into sample container 1030. When using pressurized foam container 1020, the extraction process takes only a few seconds. The foam then settles back into a liquid, and the extractor is disassembled so that sample container 1030 can be taken elsewhere for analysis of the collected particles.

Figure 11:
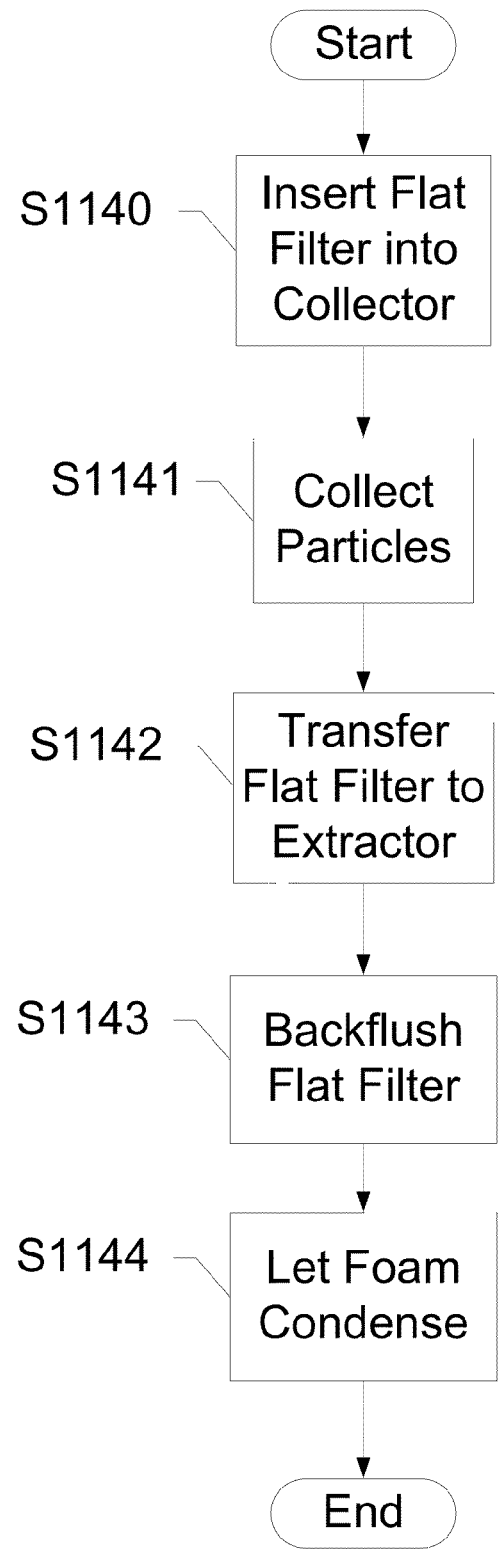
FIG. 11 shows a method of collecting and extracting particles from a flat filter, according to an exemplary embodiment of the present invention.

FIG. 11 shows a method of collecting and extracting particles from a flat filter, according to an exemplary embodiment of the present invention. First, the flat filter is inserted into the collector S1140. Next, the collector is powered and air is forced through the flat filter, resulting in a collection of particles S1141 on the surface of the flat filter. Next, the flat filter is removed from the collector and inserted into the extractor S1142 between the nozzle from the source of foam and the sample container. The flat filter should be oriented so that the side facing the aerosol chamber intake is facing the sample container. Finally, the foam backflushes the flat filter S1143 by washing foam through the flat filter and into the sample container. The foam then settles in the sample container into a small amount of liquid S1144.

The foregoing instrumentalities have significant utility in medical, environmental, or security applications. For example, collection and elution in the manner described facilitates aerosol sampling for pathogens or bioterrorism threat agents that can withstand being placed in a liquid sample for analysis. A list of such pathogens may be provided, for example, as recognized by the Center for Disease Control. These organisms may be studied using conventional techniques that are facilitated by the concentration of samples as described above:

TABLE 1

| CDC CATEGORY A AND B BIOTERRORISM AGENTS LIST |
| --- |
| CATEGORY A |

Anthrax (*Bacillus anthracis*)
Botulism (*Clostridium botulinum* toxin)
Plague (*Yersinia pestis*)
Smallpox (*Variola major*)
Tularemia (*Francisella tularensis*)

TABLE 1-continued

CDC CATEGORY A AND B BIOTERRORISM AGENTS LIST

Viral hemorrhagic fevers (filoviruses [e.g., Ebola, Marburg] and arenaviruses [e.g., Lassa, Machupo])
CATEGORY B Brucellosis (*Brucella* species)
Epsilon toxin of *Clostridium perfringens*
Food safety threats (e.g., *Salmonella* species, *Escherichia coli* O157:H7, *Shigella*)
Glanders (*Burkholderia mallei*)
Melioidosis (*Burkholderia pseudomallei*)
Psittacosis (*Chlamydia psittaci*)
Q fever (*Coxiella burnetii*)
Ricin toxin from *Ricinus communis* (castor beans)
Staphylococcal enterotoxin B
Typhus fever (*Rickettsia prowazekii*)
Viral encephalitis (alphaviruses [e.g., Venezuelan equine encephalitis, eastern equine encephalitis, western equine encephalitis])
Water safety threats (e.g., *Vibrio cholerae, Cryptosporidium parvum*)

TABLE 2

SECONDARY POTENTIAL BIOLOGICAL THREAT AGENTS

| | |
|---|---|
| Viri/prions | *Histoplasma capsulatum* |
| Flaviviruses (Yellow fever virus, West Nile virus, Dengue, Japanese Encephalitis, TBE, etc.) | *Cryptococcus neoformans* |
| | *Aspergillus niger* |
| | Pathogenic fungi |
| Hep A, B, C | *Acremomium* spp. |
| Prions (CJD, BSE, CWD) | *Alternaria alternate* |
| Alphaviruses (VEE, EEE, WEE) | *Apophysomyces elegans* |
| Nipah virus | *Aspergillus terreus* |
| Rabies virus | *Bipolaris* spp. |
| Rhinovirus (could be modified?) | *Bipolaris spicifera* |
| Polioviruses | *Blastoschizomyces capitatus* |
| Hantaviruses | *Candida krusei* |
| Filoviruses (Ebola, Marburg, Lassa) | *Candida lusitaniae* |
| Bacilli | *Cladophialophora bantiana* |
| *Mycobacterium tuberculosis*, drug resistant Mycobacteria other than TB, like *C. leprae* | *Cunnihamella berholletiae* |
| | *Curvularia lunata* |
| | *Exserohilum rostratum* |
| *Streptococcus pneumoniae* | *Fusarium moniliforme* |
| *S. pyogenes* | *Fusarium solani* |
| *S. aureus* | *Hansenula anomala* |
| *Clostridium tetani* | *Lasiodilodia theobromae* |
| *C. difficile* | *Malassezia furfur* |
| *Bacillus cereus* | *Paecilomyces lilacinus* |
| *Coxiella brunette* (Q fever) | *Paecilomyces bariotii* |
| *Francisella tularensis* | *Penicillium marneffei* |
| *Borrelia recurrentis* | *Phialemonium curvatum* |
| *Rickettsia rickettsii* | *Philophora parasitica* |
| *R. prowazekii* | *P. richardsiae* |
| *Shigella sonnei* | *Ramichloridium* spp. |
| *Bartonella henselae* | *Rhizomucor pusillus* |
| *Yersinia enterolitica* | *Rhizopus rhizopodiformus* |
| *Y. pseudotuberculosis* | *Rhodotorula rubra* |
| *Neisseria meningitidis* | *Sacchromyces cerevisiae* |
| *Legionella pneumophila* | *Scedosporium prolificans* |
| *Burkholderia pseudomallei* | *Trichosporon beigelii* (*T. asahii*) |
| *Pasturella multocida* | *Wangiella dermatitidis* |
| Other Pathogenic Microorganisms | |
| *Cryptosporidium parvum* | |

TABLE 3

PHYSICAL SIZES OF SOME AGENTS AND SURROGATES

| TARGET | PHYSICAL SIZE |
|---|---|
| *Bacillus thuringiensis* endospore | approximately 1 μm |
| *Bacillus anthracis* endospore | approximately 1 μm |

TABLE 3-continued

PHYSICAL SIZES OF SOME AGENTS AND SURROGATES

| TARGET | PHYSICAL SIZE |
|---|---|
| *Yersinia pestis* | Gram negative rod-ovoid 0.5-0.8 μm in width and 1-3 μm in length |
| *Yersinia rohdei* | approximately 1 μm |
| Venezuelan Equine Encephalitis | 70 nm (0.07 μm) |
| Gamma-killed MS2 | 2 mD or about 25 nm (0.025 μm) (but will pass through a 300 kD pore size but is retained by a 100 kD pore size Wick and McCubbin - ECBC) |
| Ovalbumin | 45 kD or 6 nm (0.006 μm) |
| Botulinum Toxoid A | 150 to 900 kD or 10 nm to 70 nm (0.01 μm to 0.07 μm)(Normally published as 150 kD however some publications state that toxoid A can be released as complexes comprised of the 150 kD toxin protein along with associated non-toxin proteins and can therefore be released in 900 kD, 500 kD, and 300 kD forms. |
| DNA | 1000 Bp or 600 kD up to 15,000 Bp or 9 mD |

The foregoing disclosure of the exemplary embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A system for extracting a sample from an aerosol, the system comprising:
 a flat filter adapted to capture aerosol floating in an air flow;
 an extractor for backflushing the flat filter with an elution foam;
 a vent for releasing a positive pressure caused by the elution foam breaking down into a liquid containing a sample; and
 a container for collecting the foam once it is backflushed through the flat filter;
 wherein the flat filter collects the sample from the aerosol, then the foam is used to backflush the flat filter into the container.

2. The system in claim 1, wherein the flat filter includes a cassette housing and a filter material.

3. The system in claim 2, wherein the filter material is one of an electrically enhanced, depth, and membrane filter material.

4. The system of claim 3, wherein the electrically enhanced filter material is an electret filter material.

5. The system in claim 4, wherein the flat filter is sealingly coupled with the aerosol chamber such that air flowing through the aerosol chamber is forced through the flat filter.

6. The system in claim 5, wherein the extractor receives the flat filter and seals it between the nozzle and the sample container.

7. The system in claim 5, wherein the source of the foam includes an elution foam solution inside a pressurized container, the pressurized container including a release valve.

8. The system of claim 3, wherein the depth filter material is one of a glass fiber, polymer fiber, and cellulose fiber filter material.

9. The system in claim 2, further comprising a collector that includes an aerosol chamber and a vacuum pump.

10. The system in claim 9, wherein the extractor includes a tube for guiding the foam from a source and a nozzle for connecting the tube to the flat filter.

11. The system in claim 1, wherein the foam is backflushed through the flat filter in an extractor.

12. A method for extracting a sample from an aerosol, the method comprising:

providing an air flow with aerosol therein;

collecting particles from the aerosol onto a flat filter;

backflushing the filter with elution foam; and releasing a positive pressure caused by the elution foam breaking down into a liquid containing the sample.

13. The method in claim 12, further comprising transferring the flat filter to an extractor.

14. The method in claim 12, wherein the backflushing takes place within the extractor.

15. A device for extracting a sample from an aerosol, the device comprising:

a filter material;

a cassette housing encasing the filter material such that the surface of the filter material is substantially exposed on both sides;

wherein the cassette housing is adapted to be sealingly inserted between a nozzle and a sample container, the nozzle for an elution foam used to backflush the flat filter into the sample container; and a vent for releasing a positive pressure caused by the elution foam breaking down into a liquid containing the sample.

16. The device in claim 15, further comprising a filter backing screen coupled to the housing on each side of the filter material.

17. The device in claim 15, wherein the filter material is one of an electrically enhanced, depth, and membrane filter material.

18. The device in claim 17, wherein the electrically enhanced filter material is an electret filter material.

19. The device in claim 17, wherein the depth filter material is one of a glass fiber, polymer fiber, or cellulose fiber material.

20. The device in claim 15, wherein the cassette housing is designed to sealingly couple with a collector such that air is forced through the filter material.

* * * * *